(12) United States Patent
Chen et al.

(10) Patent No.: US 8,308,935 B2
(45) Date of Patent: Nov. 13, 2012

(54) BIO-SENSING DEVICE CAPABLE OF AUTOMATICALLY DETECTING SENSING CODE AND SENSING METHOD THEREOF

(75) Inventors: Chun-Yu Chen, Taipei (TW); Chung-Chih Hsiao, Taipei (TW); Chung-Ping Tang, Tucheng (TW)

(73) Assignee: R3dstar Biomedical Corp. (TW)

( * ) Notice: Subject to any disclaimer, the term of this patent is extended or adjusted under 35 U.S.C. 154(b) by 433 days.

(21) Appl. No.: 12/693,419

(22) Filed: Jan. 25, 2010

(65) Prior Publication Data

US 2011/0184263 A1 Jul. 28, 2011

(51) Int. Cl.
*G01N 27/416* (2006.01)
*G01N 27/327* (2006.01)

(52) U.S. Cl. .................. 205/777.5; 204/403.02; 204/406

(58) Field of Classification Search ............. 204/403.01, 204/403.02, 403.04, 406; 205/777.5, 792
See application file for complete search history.

(56) References Cited

U.S. PATENT DOCUMENTS

| 5,126,034 | A | * | 6/1992 | Carter et al. | ............. | 204/403.05 |
| 5,266,179 | A | * | 11/1993 | Nankai et al. | ................. | 204/401 |
| 2006/0144704 | A1 | * | 7/2006 | Ghesquiere et al. | ..... | 204/403.01 |

OTHER PUBLICATIONS

Bard and Faulkner, Electrochemical Methods 2nd Ed., 2001, pp. 635 and 636.*

* cited by examiner

*Primary Examiner* — Kaj K Olsen (57) ABSTRACT

The present invention relates to a bio-sensing device capable of automatically detecting a sensing code and a sensing method thereof. The bio-sensing device has a bio-sensing strip and a process-and-display unit. The bio-sensing strip has a passive component, wherein a physical value of the passive component is able to present a sensing code. When the bio-sensing strip is inserted into the process-and-display unit, the process-and-display unit reads the sensing code to produce an appropriate compensation value of a sample. Moreover, by the sensing method, the process-and-display unit is able to detect the sensing code of the bio-sensing strip, and automatically, to access, calculate, compensate, and display the sensing code of the sample.

7 Claims, 12 Drawing Sheets

BIO-SENSING DEVICE CAPABLE OF AUTOMATICALLY DETECTING SENSING CODE AND SENSING METHOD THEREOF

BACKGROUND OF THE INVENTION

1. Technical Field

The present invention relates to bio-sensing devices, and more particularly, to a bio-sensing device capable of automatically detecting a sensing code in which a passive component is disposed on a bio-sensing strip so that a process-and-display unit can automatically detect a sensing code of the bio-sensing strip, and a sensing method thereof.

2. Description of Related Art

With rapid development of sensor technologies in recent years, various bio-sensors employing a redox reaction of ferment have been brought forward continuously, with newer ones being developed in succession to replace older ones. Among such bio-sensors, those intended for use in the bio-medical field are the most diversified, for example, blood-sugar sensors. Blood-sugar sensors are adapted to test blood-sugar content, so they have become a kind of important devices for diabetics to test their own blood-sugar content. The blood-sugar sensors can help the diabetics to detect, by themselves, blood-sugar concentration in their bodies so that the diabetics can be, at any time as desired, informed of and control blood sugar concentration in their bodies, thereby keeping the blood-sugar concentration within a normal range. Once a patient finds that the blood-sugar concentration in his or her body is too high, he or she can take such measures as dieting, exercising and insulin injection to control the blood-sugar content. However, these control measures must be adopted under supervision and suggestion of a doctor.

Figure 1:
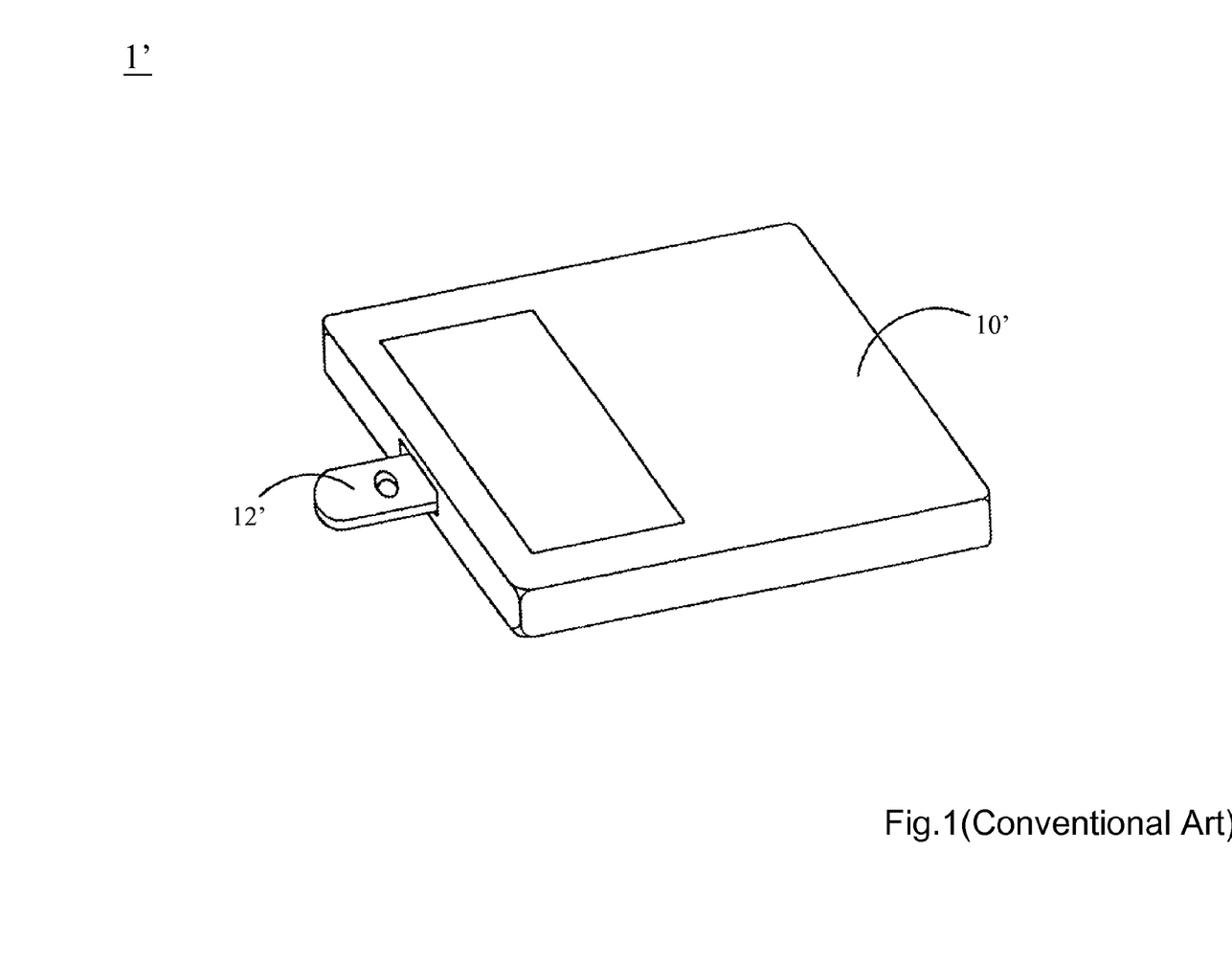
FIG. 1 is a perspective view of a conventional blood-sugar sensing device.
Figure 2:
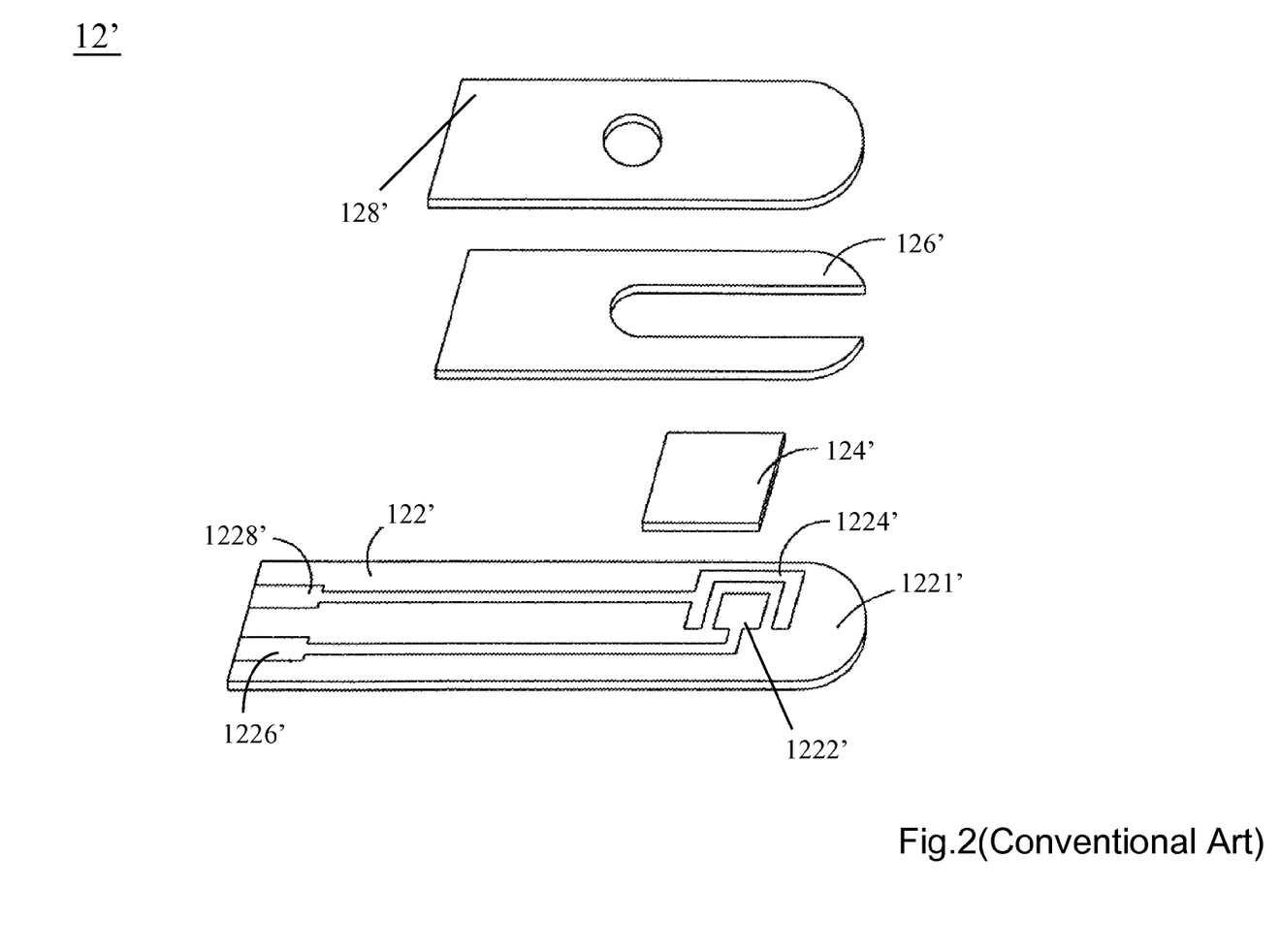
FIG. 2 is an exploded view of a conventional blood-sugar sensing strip.

Referring to FIG. 1 and FIG. 2, there are shown a perspective view of a conventional blood-sugar sensing device and an exploded view of a conventional blood-sugar sensing strip respectively. The conventional blood-sugar sensing device 1' comprises: a blood-sugar sensing strip 12' and a process-and-display unit 10'. The blood-sugar sensing strip 12' comprises: a strip substrate 122', a reaction layer 124', a spacer 126' and a cover 128'. An electrode portion 1221' is disposed at a front end of the strip substrate 122', and the reaction layer 124', the spacer 126' and the cover 128' are sequentially overlaid on the electrode portion 1221'. Moreover, a working electrode 1222' and an auxiliary electrode 1224', which are disposed on the electrode portion 1221', are electrically connected to a first conductor 1226' and a second conductor 1228' disposed at a tail end of the strip substrate 122' respectively. In addition, the reaction layer 124' overlaid on the electrode portion 1221' has enzyme contained therein for use in the redox reaction of ferment.

When using the aforesaid conventional blood-sugar sensing device 1', a diabetic first inserts the blood-sugar sensing strip 12' into the process-and-display unit 10'. Then, the patient must, first of all, input a sensing code of the blood-sugar sensing strip 12' into the process-and-display unit 10' and, afterward, take his or her own blood to drip directly onto the reaction layer 124' of the blood-sugar sensing strip 12' so as to allow an electrochemical reaction to be carried out for a period of time. In this way, the process-and-display unit 10' can calculate the blood-sugar concentration in the blood by reading variations in current generated from the electrochemical reaction.

The aforesaid conventional blood-sugar sensing device 1' is a quite practical and precise device for sensing blood-sugar concentration. However, the most prominent drawback of the blood-sugar sensing device 1' lies in that, it fails to automatically detect the sensing code of the blood-sugar sensing strip 12'. When using the conventional blood-sugar sensing device 1', the diabetic must first input the sensing code of the blood-sugar sensing strip 12' for correction of the blood-sugar concentration before dripping the blood onto the reaction layer 124'. However, in case a false sensing code is inputted by the patient, this would certainly affect accuracy of the blood-sugar concentration in the blood calculated by the process-and-display unit 10', and even more serious, cause the patient to falsely determine his or her own conditions of diabetes, resulting in an undesired consequence.

Therefore, in view of the drawbacks and shortcomings of the aforesaid conventional blood-sugar sensing device, the inventor of the present application has made great efforts to make inventive research thereon and eventually provides a bio-sensing device capable of automatically detecting a sensing code and a sensing method thereof according to the present invention.

BRIEF SUMMARY OF THE INVENTION

A primary objective of the present invention is to provide a bio-sensing device capable of automatically detecting a sensing code, in which a passive component is disposed on a bio-sensing strip to represent a sensing code so that a process-and-display unit can automatically obtain the sensing code by detecting a physical value of the passive component. Thus, the problem that the process-and-display unit would give a wrong sample magnitude value in case a false sensing code is inputted by a user can be avoided.

The other primary objective of the present invention is to provide a sensing method for the bio-sensing device, which enables the process-and-display unit to, apart from automatically detecting the sensing code of the bio-sensing strip, read, calculate, compensate and display an accurate sample magnitude value.

Accordingly, to achieve the primary objective of the present invention, the inventor of the present application proposes the bio-sensing device capable of automatically detecting a sensing code, which comprises a bio-sensing strip and the process-and-display unit. The bio-sensing strip comprises: a first electrode having enzyme contained reagent matrix therein to react with a sample; a second electrode having the enzyme contained therein to react with the sample; a passive component, having an end thereof connected to the first electrode and having a physical value that can represent the sensing code of the bio-sensing strip; and a third electrode being connected to the other end of the passive component so that the passive component can be electrically connected to an electronic circuit. The process-and-display unit comprises: a detection circuit being electrically connectible to the bio-sensing strip to detect the physical value of the passive component and convert the physical value into a first digital signal; a read circuit being electrically connectible to the bio-sensing strip to read an electrochemical reaction signal and convert the electrochemical reaction signal into a second digital signal; a microprocessor being electrically connected to the detection circuit and the read circuit and configured to verify the sensing code of the bio-sensing strip by processing the first digital signal and further set an appropriate compensation value, and configured to receive the second digital signal to process the second digital signal into a sample measurement value, and configured to numerically compensate the sample measurement value based on the appropriate compensation value so as to output an accurate sample magnitude value; and a display member being electrically connected to the microprocessor to display the accurate sample magnitude value.

To achieve the other objective of the present invention, the inventor of the present application proposes the sensing method for the bio-sensing device, which comprises the following steps of: (1) inserting a bio-sensing strip having a passive component into the process-and-display unit; (2) enabling the process-and-display unit to activate a detection circuit therein; (3) enabling the detection circuit to detect a physical value of the passive component and convert the physical value into a first digital signal; (4) enabling a microprocessor to receive the first digital signal to verify a sensing code of the bio-sensing strip; (5) enabling the microprocessor to further set an appropriate compensation value according to the sensing code; (6) dripping a sample onto enzyme contained reagent matrix of the bio-sensing strip; (7) enabling the process-and-display unit to activate a read circuit therein; (8) enabling the read circuit to read an electrochemical reaction signal representing an electrochemical reaction of the sample with the enzyme contained reagent matrix and convert the electrochemical reaction signal into a second digital signal; (9) enabling the microprocessor to receive the second digital signal and process the second digital signal into a sample measurement value; and (10) enabling the microprocessor to numerically compensate the sample measurement value based on the appropriate compensation value so as to obtain and output an accurate sample magnitude value.

BRIEF DESCRIPTION OF THE SEVERAL VIEWS OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE INVENTION

To more clearly describe a bio-sensing device capable of automatically detecting a sensing code and a sensing method thereof according to the present invention, preferable embodiments of the present invention will be described in detail with reference to the attached drawings.

Figure 3:
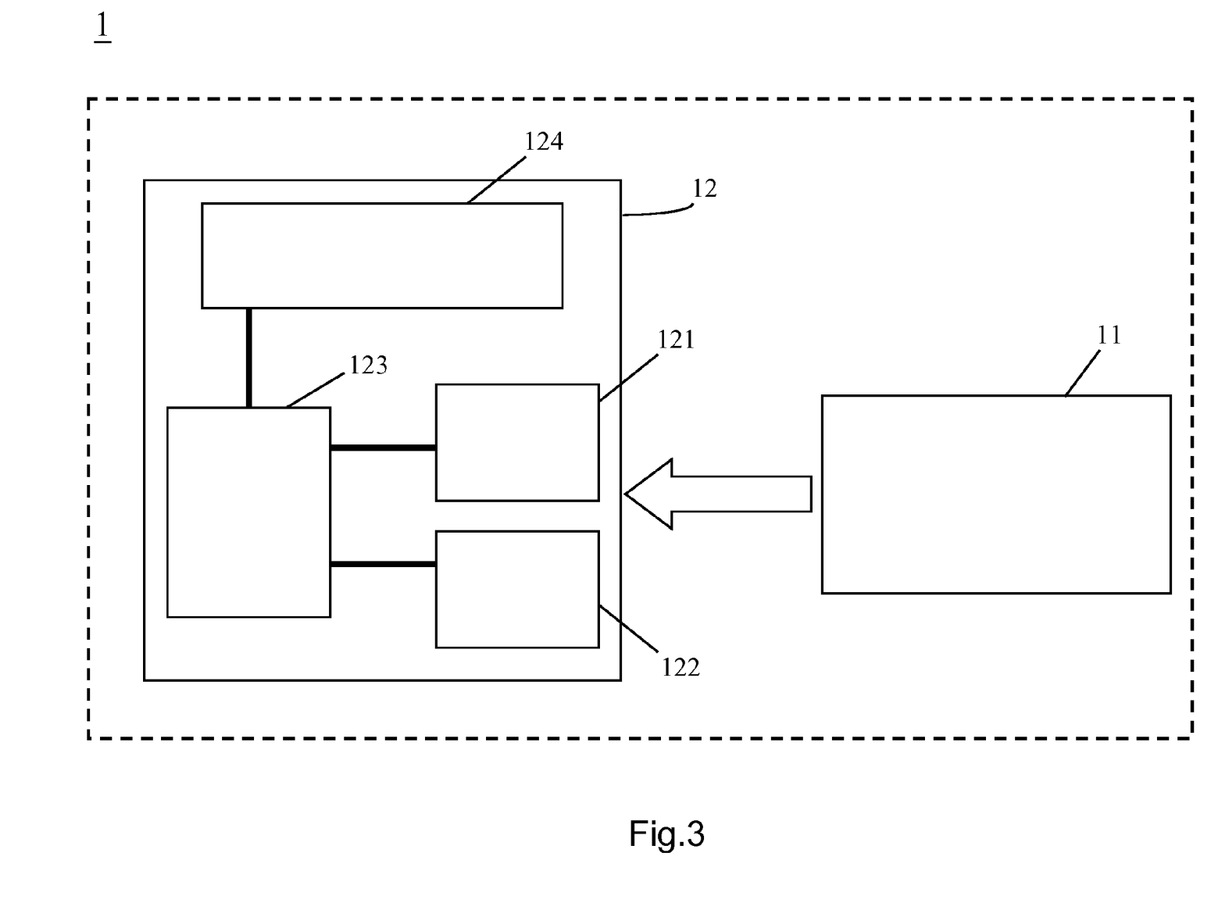
FIG. 3 is an architecture view of a bio-sensing device capable of automatically detecting a sensing code according to the present invention.

Referring to FIG. 3, there is shown an architecture view of a bio-sensing device capable of automatically detecting a sensing code of the present invention. The bio-sensing device 1 capable of automatically detecting a sensing code comprises a bio-sensing strip 11 and a process-and-display unit 12.

Figure 4:
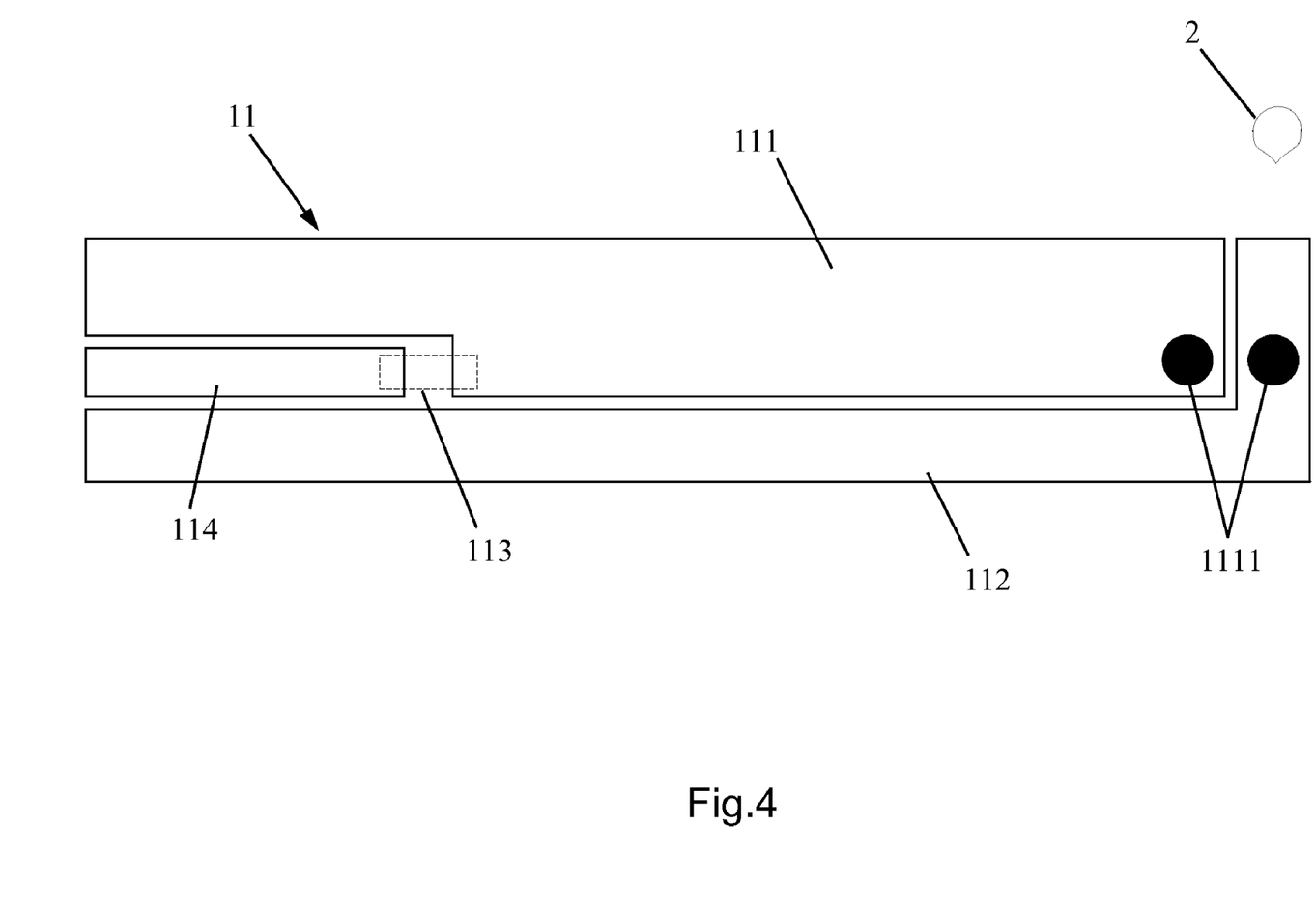
FIG. 4 is a top view of a bio-sensing strip of the bio-sensing device capable of automatically detecting a sensing code.

Referring to FIG. 3 and FIG. 4 together, wherein FIG. 4 is a top view of the bio-sensing strip, the bio-sensing strip 11 comprises: a first electrode 111, which is electrically connectible to an electronic circuit in the process-and-display unit 12 and having enzyme 1111 contained therein to react with a sample 2; a second electrode 112 being electrically connectible to the electronic circuit in the process-and-display unit 12 and having the enzyme 1111 contained therein to react with the sample 2; a passive component 113, which has an end thereof connected to the first electrode 111 and having a physical value representing a sensing code of the bio-sensing strip 11, wherein the passive component 113 may be a resistor, a capacitor or an inductor; and a third electrode 114 being connected to the other end of the passive component 113 so that the passive component 113 can be electrically connected to the electronic circuit. In this embodiment, the first electrode 111 is a working electrode, and the second electrode 112 is a counter electrode corresponding to the working electrode, while the third electrode 114 is a sensing code electrode for connection with the passive component 113.

Referring next to FIG. 3, the process-and-display unit 12 comprises: a detection circuit 121, which is electrically connectible to the bio-sensing strip 11 to detect the physical value of the passive component 113 and convert the physical value into a first digital signal; a read circuit 122 being electrically connectible to the bio-sensing strip 11 to read an electrochemical reaction signal representing an electrochemical reaction of the sample 2 with the enzyme contained reagent matrix 1111 and convert the electrochemical reaction signal into a second digital signal; a microprocessor 123, which is electrically connected to the detection circuit 121 and the read circuit 122 and configured to verify the sensing code of the bio-sensing strip 11 by processing the first digital signal and to further set an appropriate compensation value, configured to receive the second digital signal and process the second digital signal into a sample measurement value, and configured to numerically compensate the sample measurement value based on the appropriate compensation value so as to output an accurate sample magnitude value; and a display member 124 being electrically connected to the microprocessor 123 to display the sample magnitude value. The display member 124 may be an LCD display or an LED display, and preferably, the LCD display is adopted as the display member 124 of the process-and-display unit 12 in this embodiment.

Figure 5:
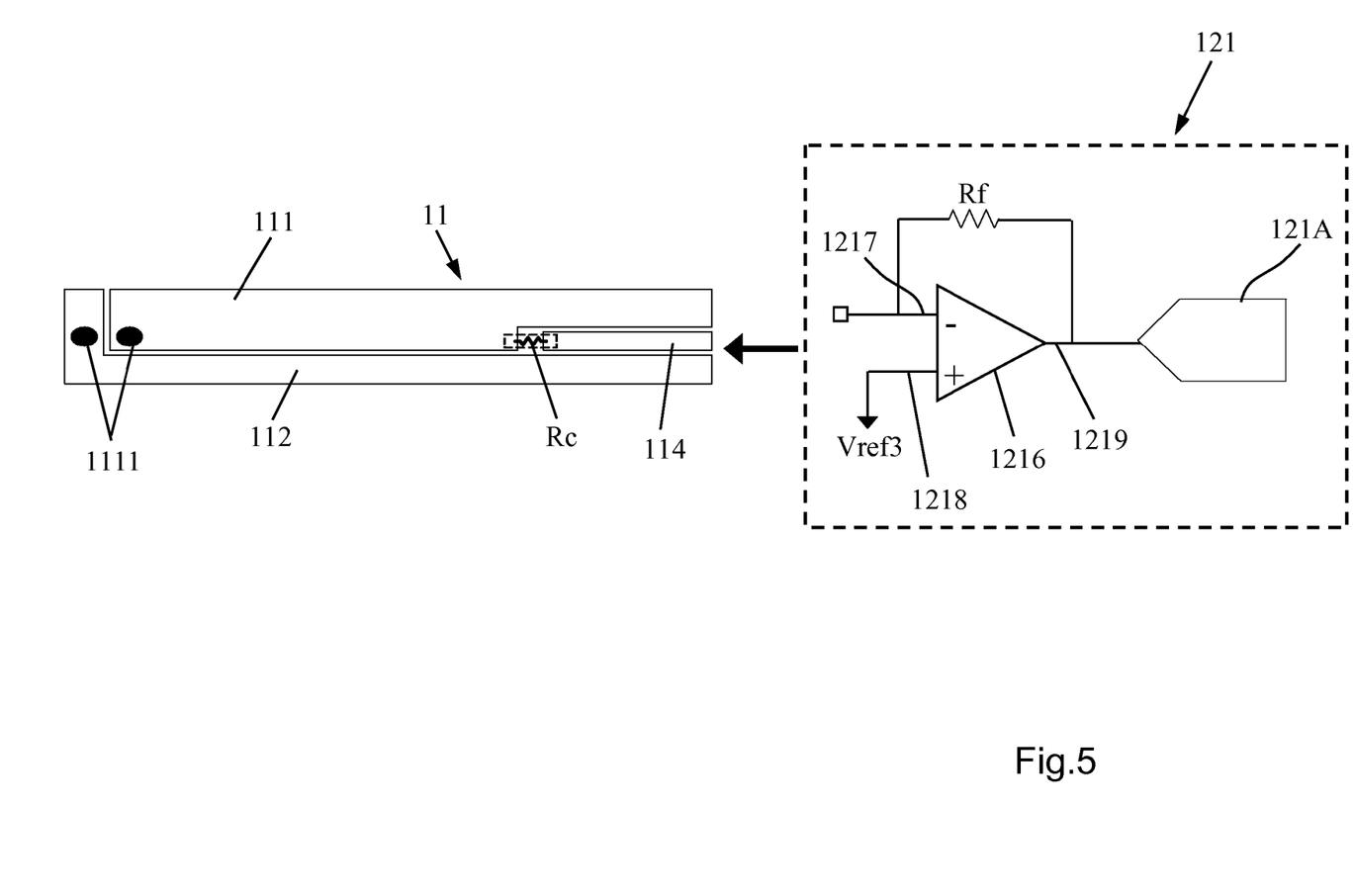
FIG. 5 is a first circuit architecture view of a detection circuit of the bio-sensing device capable of automatically detecting a sensing code.

Referring next to FIG. 5 together, there is shown a first circuit architecture view of the detection circuit. The detection circuit 121 of the process-and-display unit 12 has two kinds of circuit architectures for detecting the physical value of different passive components 113 respectively. As shown in FIG. 5, when the passive component 113 is a sensing code resistor Rc, the detection circuit 121 is configured to detect a physical value of the sensing code resistor Rc, namely, a resistance value Rp, where Rp is a symbol for formulization but not a component symbol. The detection circuit 121 comprises a second operational amplifier 1216, a conversion resistor Rf and a second A/D converter 121A. The second operational amplifier 1216 has a second amplifier negative input terminal 1217, a second amplifier positive input terminal 1218 and a second amplifier output terminal 1219. The second operational amplifier 1216 is configured to convert the physical value of the passive component 113 into a first voltage signal which has a first voltage value Vout, where Vout is a symbol for formulization but not a component symbol. The conversion resistor Rf is coupled between the second amplifier negative input terminal 1217 and the second amplifier output terminal 1219 to assist in converting the physical value of the passive component 113 into the first voltage signal. The second A/D converter 121A is coupled to the second amplifier output terminal 1219 to receive the first voltage signal and convert the first voltage signal into the first digital signal. As the second amplifier positive input terminal 1218 is coupled to a third reference voltage Vref3, the resistance value Rp can be calculated through a formula of $Rp=(Vref3 \times Rf)/(Vout-Vref3)$ to represent the sensing code.

Figure 6:
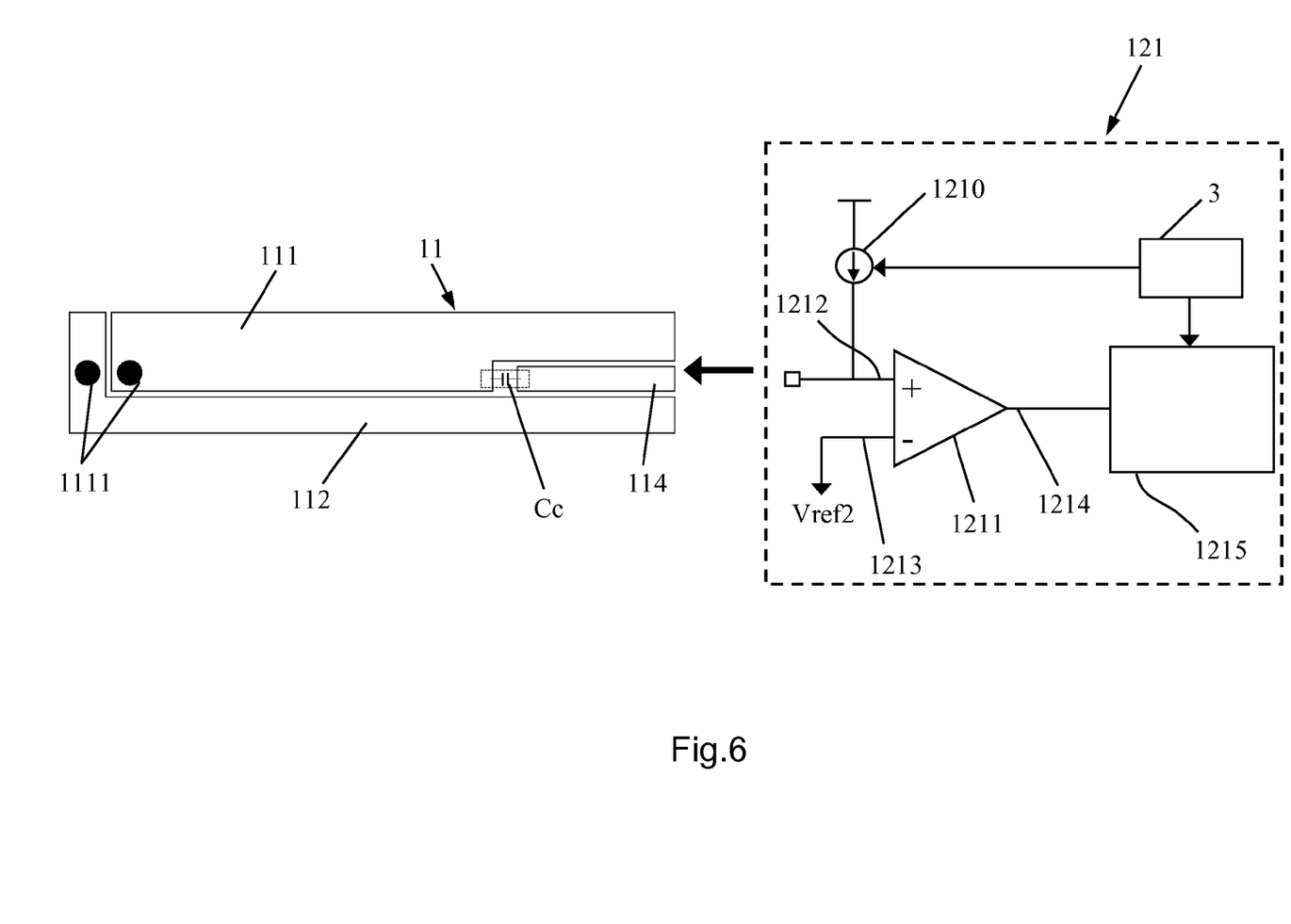
FIG. 6 is a second circuit architecture view of the detection circuit.
Figure 7:
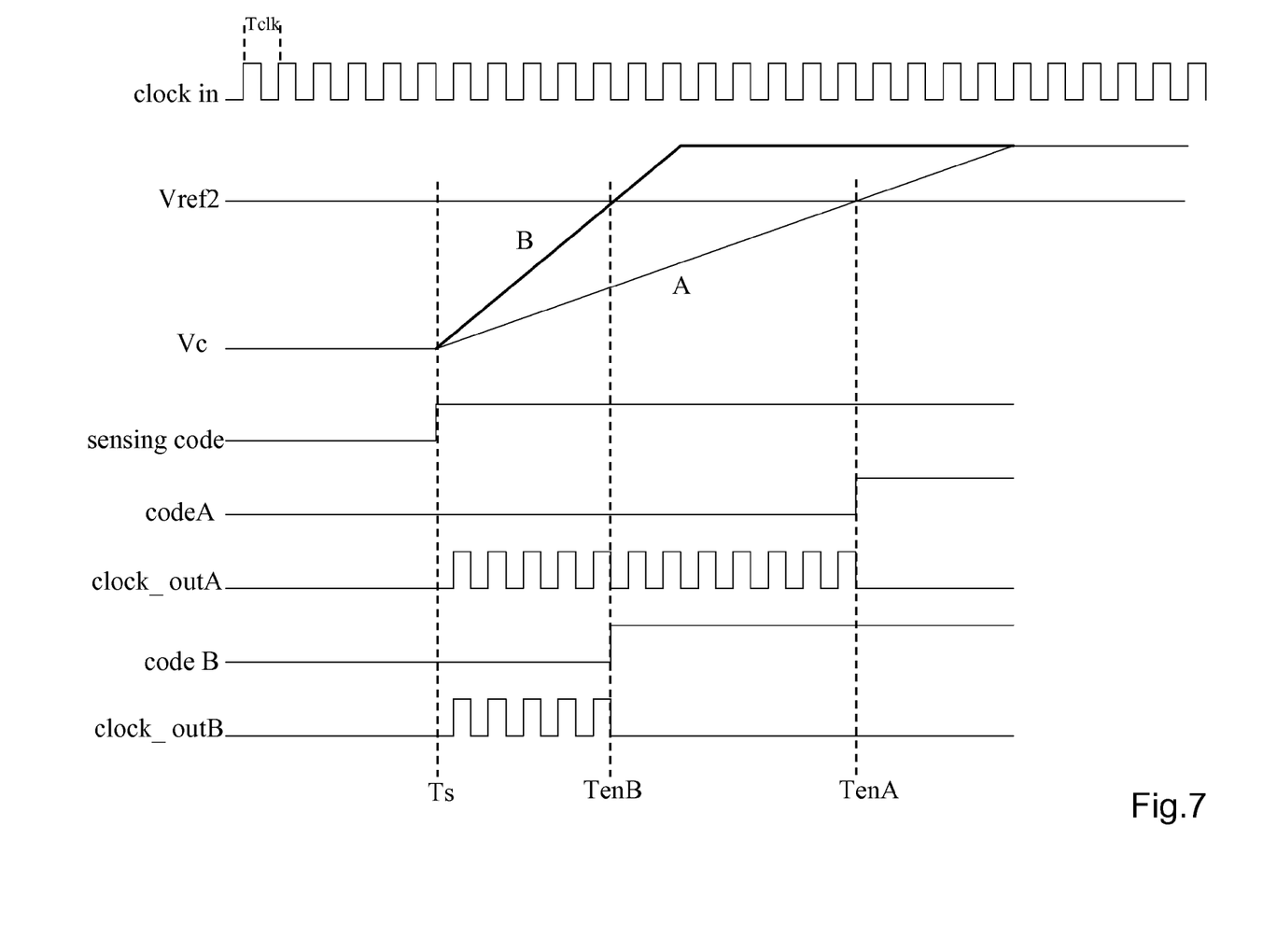
FIG. 7 is a timing diagram of charging a sensing code capacitor of the bio-sensing device capable of automatically detecting a sensing code.

Referring to FIG. 6 together, there is shown a second circuit architecture view of the detection circuit. If the passive component 113 is not a sensing code resistor Rc but a sensing code capacitor Cc, the detection circuit 121 must be configured to detect a physical value of the sensing code capacitor Cc, namely, a capacitance value Cp, where Cp is a symbol for formulization. The detection circuit 121 configured to detect the capacitance value Cp comprises a current source 1210, a comparator 1211 and a counter 1215. The current source 1210 is adapted to charge the sensing code capacitor Cc to generate a charging voltage Vc, where Vc is a symbol for formulization but not a component symbol, across the sensing code capacitor Cc. The comparator 1211 comprises a comparator positive input terminal 1212, a comparator negative input terminal 1213 and a comparator output terminal 1214. The comparator negative input terminal 1213 is coupled to a second reference voltage Vref2, and the comparator positive input terminal 1212 is coupled to the sensing code capacitor Cc. The comparator 1211 is configured to compare the charging voltage Vc with the second reference voltage Vref2 and output a high-level signal when a value of the charging voltage Vc is higher than that of the second reference voltage Vref2. The counter 1215 is coupled to the microprocessor 123, the comparator 1211 and an activation signal 3. Referring to FIG. 7 together, there is shown a timing diagram of charging the sensing code capacitor. When the activation signal 3 is set to a high level, the current source 1210 charges the sensing code capacitor Cc and, meanwhile, the counter 1215 starts counting. This proceeds until the comparator 1211 outputs the high-level signal to the counter 1215, at which moment the counter 1215 stops counting and records a count value N, where N is a symbol for formulization. As shown in FIG. 7, a curve A and a curve B represent charging voltages Vc of the sensing code capacitor Cc having different capacitance values Cp respectively; Ts represents a starting time when the counter 1215 starts counting; TenA and TenB represent a time when the counter 1215 stops counting respectively; clock_in represents an input clock signal; Tclk represents a time period of the input clock signal; and codeA and codeB represent signals outputted by the comparator 1211 after receiving the charging voltages Vc of the curve A and the curve B and comparing them with the second reference voltage Vref2, wherein codeA transits to a high-level signal at the time point of TenA and codeB transits to a high-level signal at the time point of TenB. Furthermore, clock_outA and clock_outB represent signals outputted by the counter 1215 to the microprocessor 123, from which the count values N of the charging time of the curve A and the curve B can be calculated by the microprocessor. As the value of the charging voltage Vc is equal to a current value Ic, where Ic is a symbol for formulization but not a component symbol, of the current source 1210 multiplied by the charging time of the sensing code capacitor Cc and then divided by the capacitance value Cp, the capacitance value Cp can be calculated through a formula of $Cp=(N \times Tclk \times Ic)/Vc$ to represent the sensing code.

Figure 8:
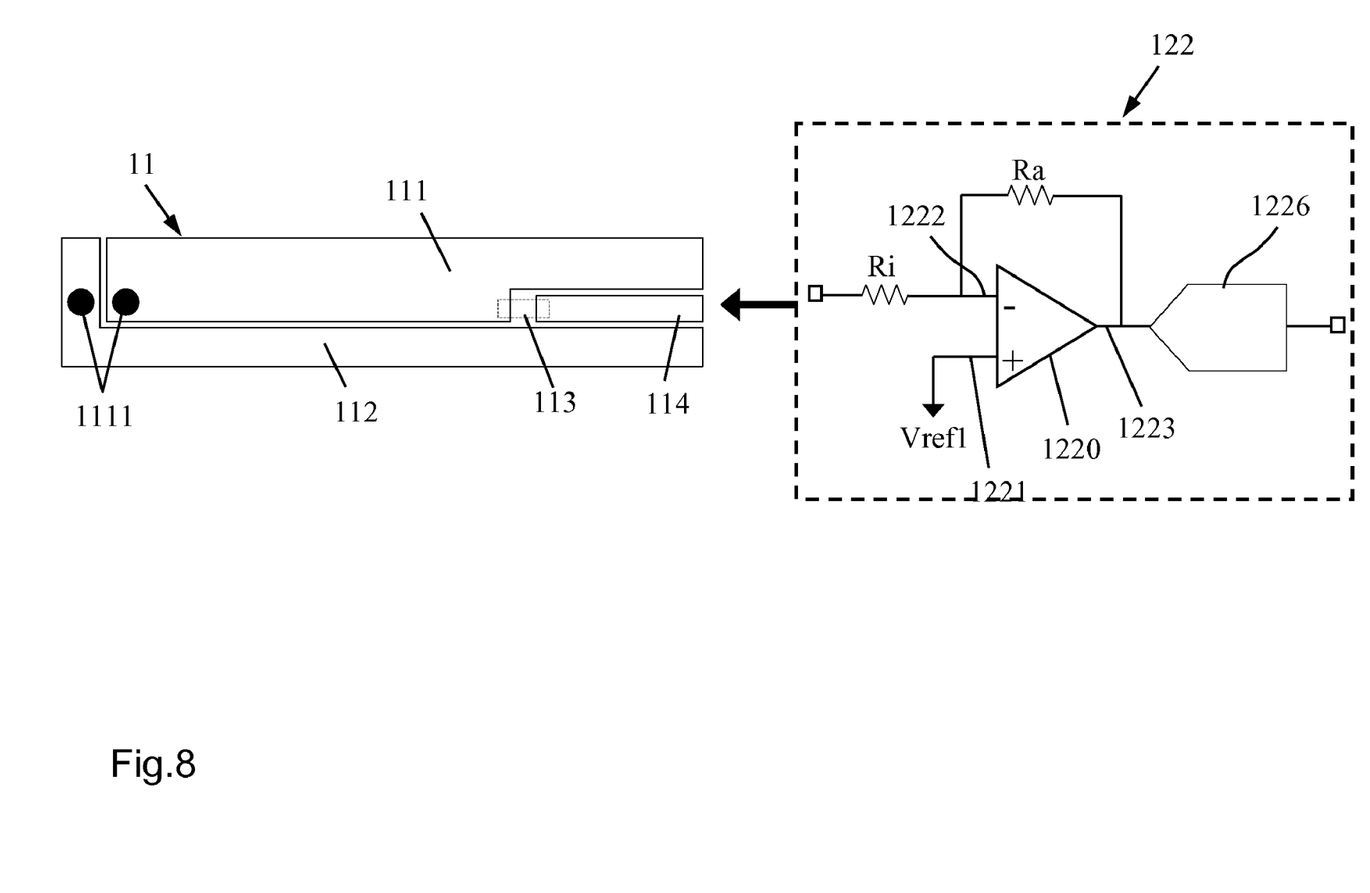
FIG. 8 is an architecture view of a read circuit of the bio-sensing device capable of automatically detecting a sensing code.

Referring next to FIG. 8 together, there is shown an architecture view of a read circuit. The read circuit 122 comprises a first operational amplifier 1220, an input resistor Ri, an amplifying resistor Ra and a first A/D converter 1226. The first operational amplifier 1220 has a first amplifier positive input terminal 1221, a first amplifier negative input terminal 1222 and a first amplifier output terminal 1223. The first amplifier positive input terminal 1221 is coupled to a first reference voltage Vref1. The first operational amplifier 1220 is configured to read the electrochemical reaction signal and convert the electrochemical reaction signal into a second voltage signal. The input resistor Ri is coupled to the first amplifier negative input terminal 1222 for use as an input buffering resistor of the first operational amplifier 1220. The amplifying resistor Ra is coupled between the first amplifier negative input terminal 1222 and the first amplifier output terminal 1223 to assist in amplifying an output gain of the first operational amplifier 1220. The first A/D converter 1226 is coupled to the first amplifier output terminal 1223 to receive the second voltage signal and convert the second voltage signal into the second digital signal. Afterwards, the microprocessor 123 receives the second digital signal to process it into the sample measurement value so that, after an appropriate compensation is made on the sample measurement value, an accurate sample magnitude value can be displayed by the display member 124.

Figure 9:
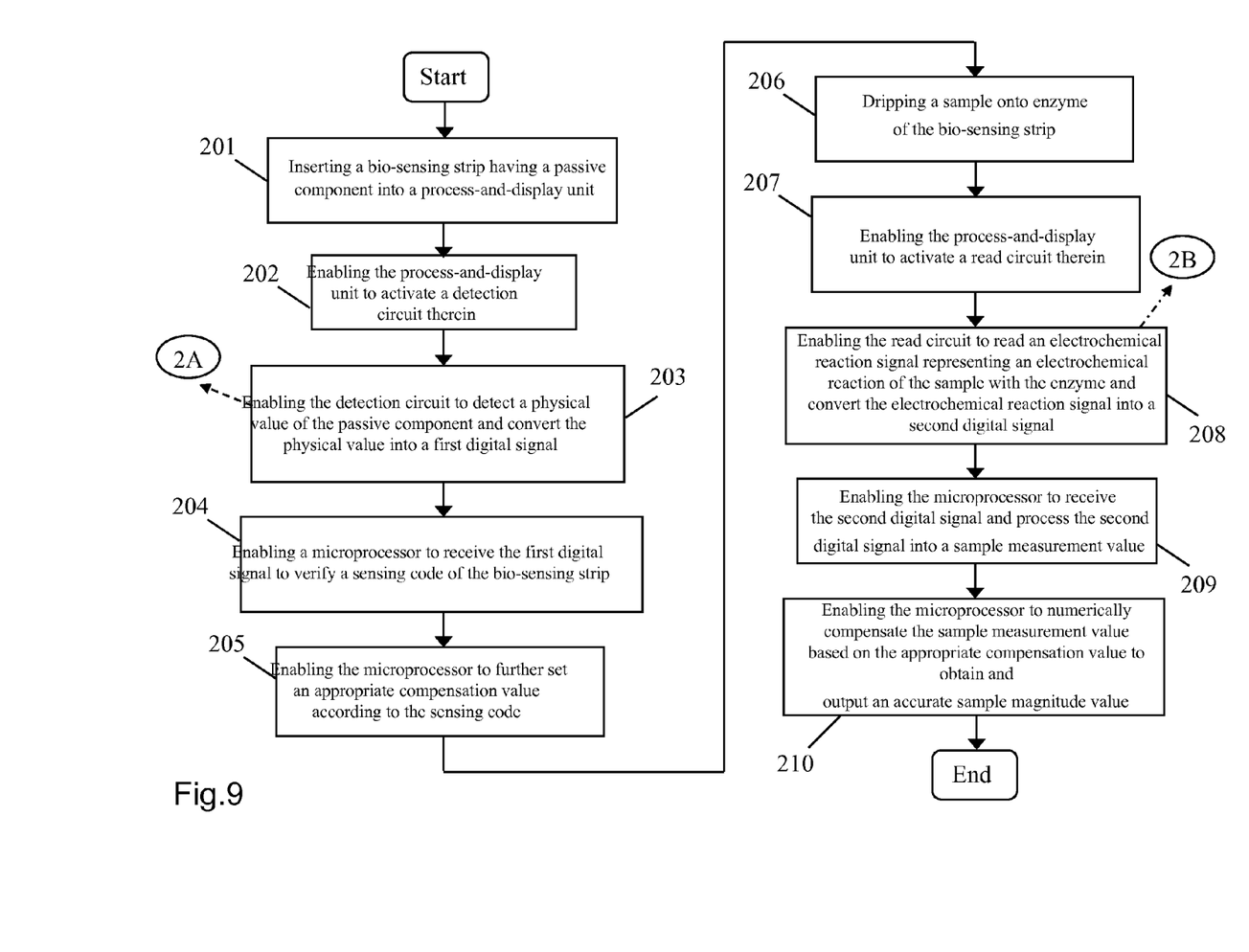
FIG. 9 is a flowchart of a sensing method for a bio-sensing device.

Thus, a preferable embodiment of the bio-sensing device 1 capable of automatically detecting a sensing code has been disclosed above very thoroughly. Furthermore, a sensing method for the bio-sensing device will be disclosed thoroughly herein below. The sensing method is used to control the bio-sensing device 1 capable of automatically detecting a sensing code so that the bio-sensing device can accomplish sensing and magnitude value calculation of the sample 2. Referring to FIG. 9 together, there is shown a flowchart of the sensing method for a bio-sensing device. The sensing method for the bio-sensing device comprises the following steps.

Firstly, step (201) is executed to insert the bio-sensing strip 11 having the passive component 113 into the process-and-display unit 12; next, step (202) is executed to enable the process-and-display unit 12 to activate the detection circuit 121 therein; then, step (203) is executed to enable the detection circuit 121 to detect the physical value of the passive component 113 and convert the physical value into the first digital signal; then step (204) and step (205) are executed to enable the microprocessor 123 to receive the first digital signal so as to verify the sensing code of the bio-sensing strip 11, and to enable the microprocessor 123 to further set the appropriate compensation value according to the sensing code; once the sensing code is obtained, sensing and testing of the sample 2 (i.e., step (206)) can be started by dripping the sample 2 onto the enzyme contained reagent matrix 1111 of the bio-sensing strip 11; then, step (207) is executed to enable the process-and-display unit 12 to activate the read circuit 122 therein; thereafter, step (208) is executed to enable the read circuit 122 to read the electrochemical reaction signal from the sample 2 and the enzyme contained reagent matrix 1111 and convert the electrochemical reaction signal into the second digital signal; subsequently, step (209) is executed to enable the microprocessor 123 to receive the second digital signal and process the second digital signal into the sample measurement value; and finally, step (210) is executed to enable the microprocessor 123 to numerically compensate the sample measurement value based on the appropriate compensation value so as to obtain and output the accurate sample magnitude value.

Figure 10:
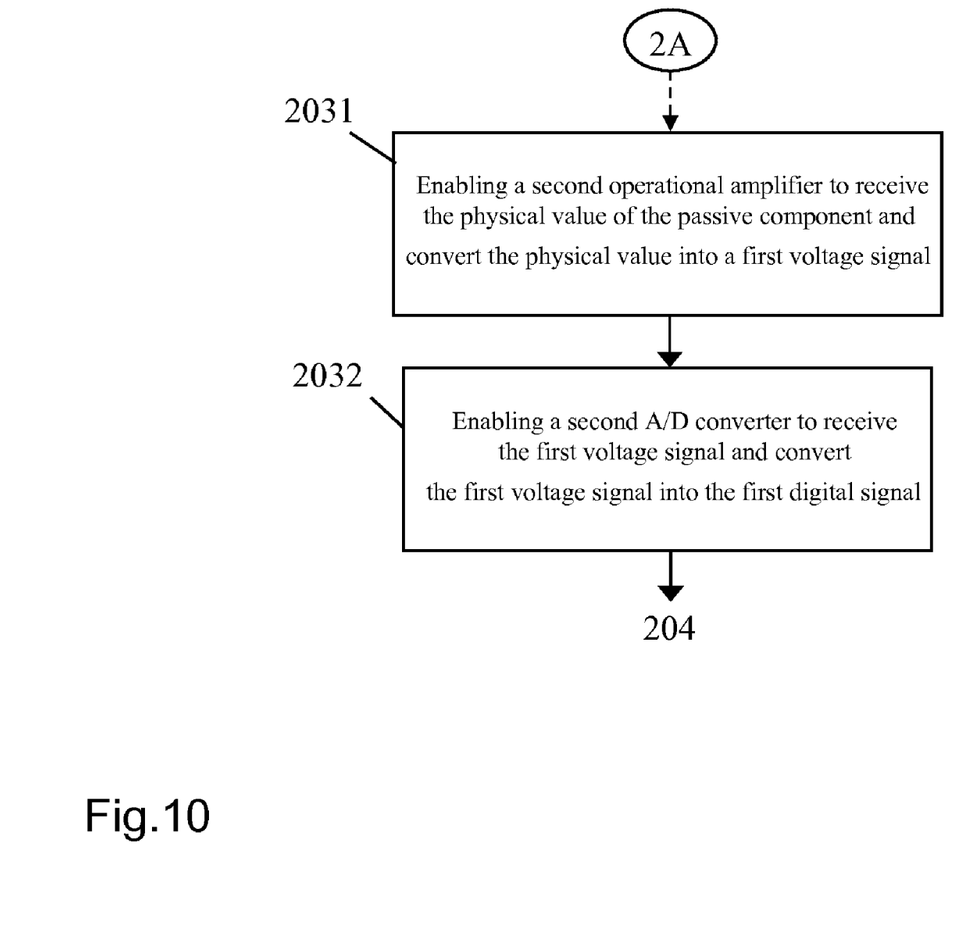
FIG. 10 is a flowchart of a first set of detailed sub-steps of step (203)

The aforesaid step (203) is a step for enabling the detection circuit 121 to detect the physical value of the passive component 113. However, if the passive component 113 is the sensing code resistor Rc, the first circuit architecture of the detection circuit 121 must be used to read the resistance value Rp of the sensing code resistor Rc. Referring to FIG. 10, there is shown a flowchart of a first set of detailed sub-steps of step (203). Specifically, step (203) comprises the following set of detailed sub-steps.

Firstly, step (2031) is executed to enable the second operational amplifier 1213 to receive the physical value of the passive component 113 and convert the physical value into the first voltage signal; and then, step (2032) is executed to enable the second A/D converter 1217 to receive the first voltage signal and convert the first voltage signal into the first digital signal.

Figure 11:
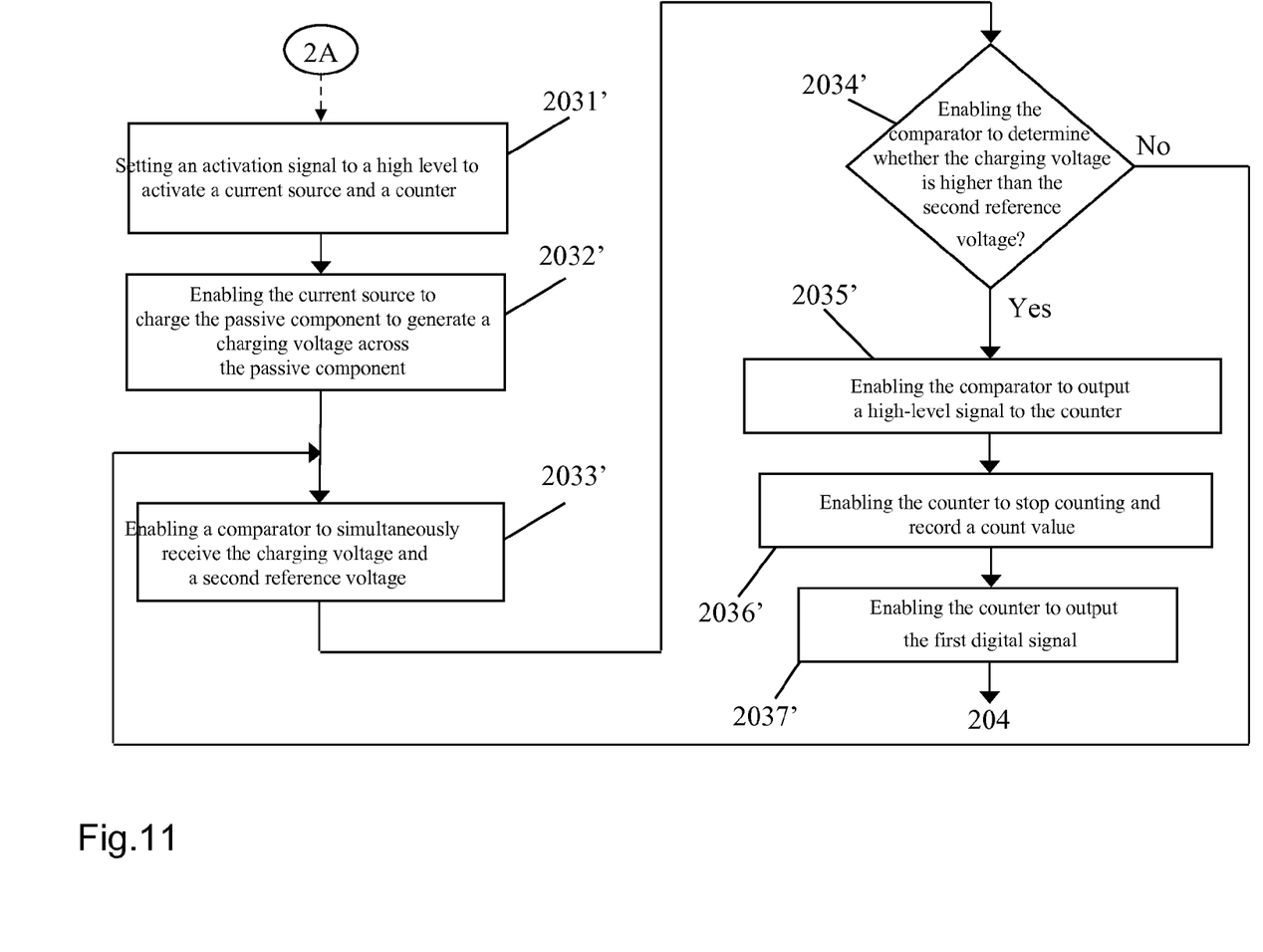
FIG. 11 is a flowchart of a second set of detailed sub-steps of step (203)

On the other hand, if the passive component 113 is the sensing code capacitor Cc, the second circuit architecture of the detection circuit 121 must be used to read the charging voltage Vc of the sensing code capacitor Cc so that the microprocessor 123 can calculate the capacitance value Cp. Referring to FIG. 11, there is shown a flowchart of a second set of detailed sub-steps of step (203). The aforesaid step (203) comprises the following second set of detailed sub-steps.

Firstly, step (2031') is executed to set the activation signal to a high level so as to activate the current source 1210 and the counter 1215; next, step (2032') is executed to enable the current source 1210 to charge the passive component 113 (i.e., the sensing code capacitor Cc) to generate the charging voltage Vc across the passive component 113; then, step (2033') is executed to enable the comparator 1211 to simultaneously receive the charging voltage Vc and the second reference voltage Vref2; thereafter, step (2034') is executed to enable the comparator 1211 to determine whether the charging voltage Vc is higher than the second reference voltage Vref2 or not; if yes, step (2035') and step (2036') are executed to enable the comparator 1211 to output a high-level signal to the counter 1215, and then enable the counter 1215 to stop counting and record a count value N; and afterwards, step (2037') is executed to enable the counter 1215 to output the first digital signal; additionally, if the answer in step (2034') is "not", step (2033') is then executed to enable the comparator 1211 to continue to receive the charging voltage Vc and the second reference voltage Vref2.

Figure 12:
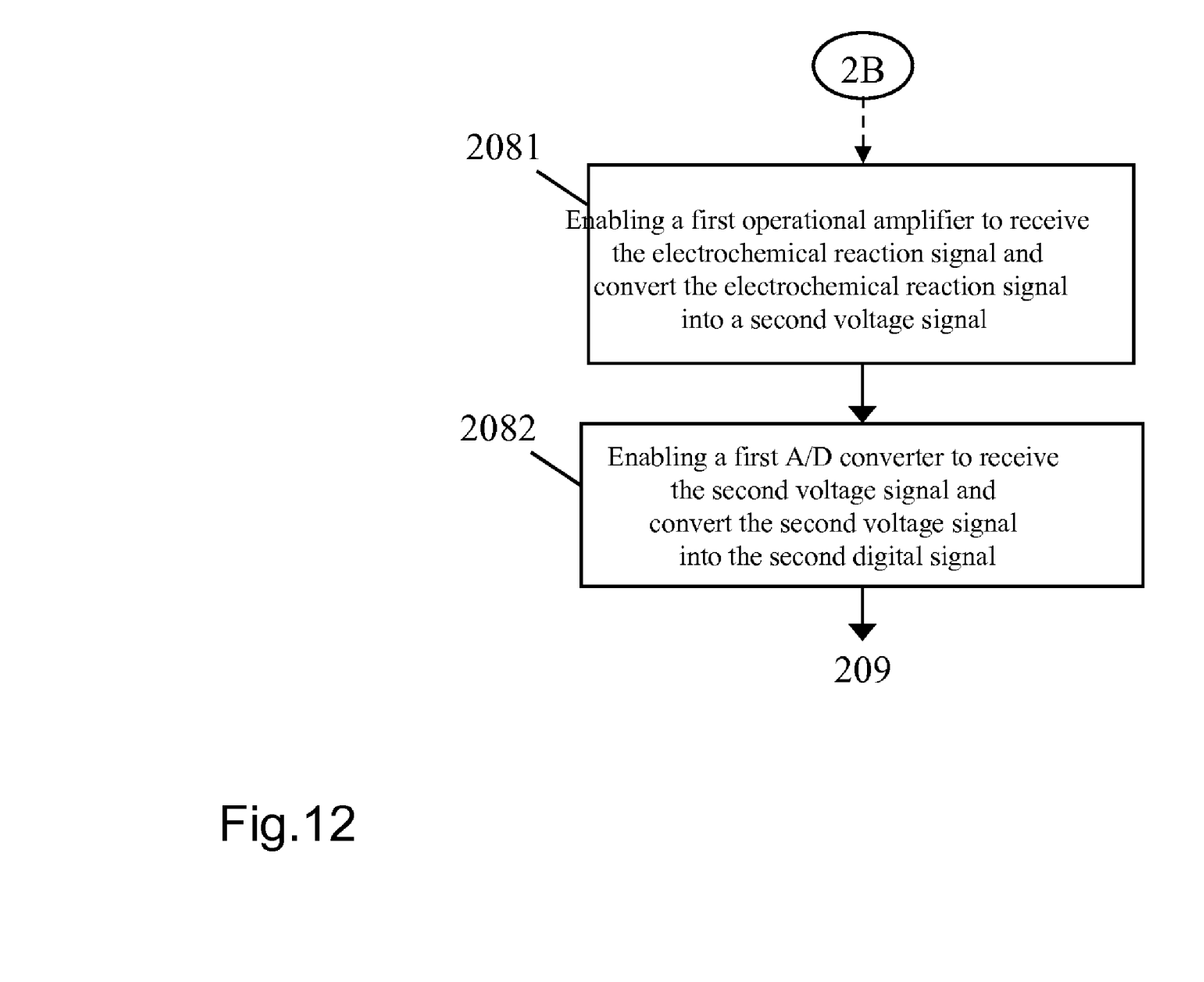
FIG. 12 is a flowchart of detailed sub-steps of step (208).

Finally, referring to FIG. 12, there is shown a flowchart of detailed sub-steps of step (208). Step (208) is a step for enabling the read circuit 122 to read the electrochemical reaction signal. Step (208) comprises the following detailed sub-steps:

Firstly, step (2081) is executed to enable the first operational amplifier 1220 to receive the electrochemical reaction signal and convert the electrochemical reaction signal into the second voltage signal; and then step (2082) is executed to enable the first A/D converter 1226 to receive the second voltage signal and convert the second voltage signal into the second digital signal.

Thus, a bio-sensing device capable of automatically detecting a sensing code and a sensing method thereof according to the present invention have been disclosed above thoroughly and clearly. In summary, as can be seen, the present invention has the following advantages:

1. According to the present invention, the passive component is disposed on the bio-sensing strip and the detection circuit is additionally disposed on the process-and-display unit to detect the physical value of the passive component, so that the sensing code can be automatically obtained and the appropriate compensation value can be calculated to numerically compensate the sample measurement value. Thereby, the problem that the process-and-display unit would give a wrong sample magnitude value in case a false sensing code is inputted by a user (a diabetic) can be avoided.

2. By means of the sensing method for a bio-sensing device, the process-and-display unit is able to automatically detect the sensing code of the bio-sensing strip, and to read, calculate, compensate and display an accurate sample magnitude value.

We claim:

1. A bio-sensing device capable of automatically detecting a sensing code, the bio-sensing device comprising:
    a bio-sensing strip comprising:
        a first electrode being electrically connectible to an electronic circuit and having enzyme contained thereon to react with a sample;
        a second electrode being electrically connectible to the electronic circuit and having the enzyme contained thereon to react with the sample;
        a capacitor having an end thereof connected to the first electrode and having a capacitance value that is able to represent a sensing code of the bio-sensing strip; and
        a third electrode being connected to the other end of the capacitor, so that the capacitor is able to be electrically connected to the electronic circuit; and
    a process-and-display unit being configured to quantitate an electrochemical reaction signal representing an electrochemical reaction of the sample with the enzyme contained reagent matrix, the process-and-display unit comprising:
        a detection circuit being electrically connectible to the bio-sensing strip to detect the physical value of the capacitor and configured to convert the physical value into a first digital signal;
        a read circuit being electrically connectible to the bio-sensing strip to read the electrochemical reaction signal representing the electrochemical reaction of the sample with the enzyme contained reagent matrix and configured to convert the electrochemical reaction signal into a second digital signal;
        a microprocessor being electrically connected to the detection circuit and the read circuit and configured to verify the sensing code of the bio-sensing strip by processing the first digital signal and further set an appropriate compensation value, configured to receive the second digital signal and process the second digital signal into a sample measurement value, and configured to numerically compensate the sample measurement value based on the appropriate compensation value to output an accurate sample magnitude value; and
        a display member being electrically connected to the microprocessor to display the accurate sample magnitude value;
    wherein the detection circuit having:
        a current source being adapted to charge the capacitor to generate a charging voltage;

a comparator comprising a comparator positive input terminal, a comparator negative input terminal and a comparator output terminal, where the comparator negative input terminal is coupled to a reference voltage and the comparator positive input terminal is coupled to the capacitor; therefore the comparator is configured to compare the charging voltage of the capacitor with the reference voltage, and then outputs a high-level signal when the charging voltage value is higher than that of the reference voltage; and a counter being coupled to the microprocessor, the comparator and an activation signal, wherein when the activation signal is set to a high level, the current source charging the capacitor and, meanwhile, the counter starting to count until the comparator outputs the high-level signal to the counter, and then the counter stops counting and records a count value.

2. The bio-sensing device of claim 1, wherein the first electrode is a working electrode, and the second electrode is a counter electrode corresponding to the working electrode, and the third electrode is a sensing code electrode for connection with the passive component.

3. The bio-sensing device of claim 1, wherein the sample is blood.

4. The bio-sensing device of claim 1, wherein the display member is any of an LCD display and an LED display.

5. The bio-sensing device of claim 1, wherein the read circuit further comprises:

an operational amplifier having a first amplifier positive input terminal, a first amplifier negative input terminal and a first amplifier output terminal, wherein the first amplifier positive input terminal is coupled to another reference voltage, and the operational amplifier is configured to read the electrochemical reaction signal and convert the electrochemical reaction signal into a second voltage signal;

an input resistor being coupled to the first amplifier negative input terminal for use as an input buffering resistor of the operational amplifier;

a amplifying resistor, being coupled between the first amplifier negative input terminal and the first amplifier output terminal to assist in amplifying an output gain of the operational amplifier; and a first A/D converter being coupled to the first amplifier output terminal to receive the second voltage signal and configured to convert the second voltage signal into the second digital signal.

6. A sensing method for a bio-sensing device, comprising:
(1) inserting a bio-sensing strip having a capacitor into a process-and-display unit of the bio-sensing device;
(2) enabling the process-and-display unit to activate a detection circuit thereon;
(3) enabling the detection circuit to detect a physical value of the capacitor and convert the physical value into a first digital signal;
(31) setting an activation signal to a high level to activate a current source and a counter;
(32) enabling the current source to charge the capacitor to generate a charging voltage;
(33) enabling a comparator to receive the charging voltage and a reference voltage simultaneously;
(34) enabling the comparator to determine whether the charging voltage is higher than the reference voltage, if yes, the step (35) will be executed and if not, the step (33) will be executed;
(35) enabling the comparator to output a high-level signal to the counter;
(36) enabling the counter to stop counting and record a count value;
(4) enabling a microprocessor to receive the first digital signal to verify a sensing code of the bio-sensing strip;
(5) enabling the microprocessor to further set an appropriate compensation value according to the sensing code;
(6) dripping a sample onto enzyme contained reagent matrix of the bio-sensing strip;
(7) enabling the process-and-display unit to activate a read circuit thereon;
(8) enabling the read circuit to read an electrochemical reaction signal representing an electrochemical reaction of the sample with the enzyme contained reagent matrix and convert the electrochemical reaction signal into a second digital signal;
(9) enabling the microprocessor to receive the second digital signal and process the second digital signal into a sample measurement value; and
(10) enabling the microprocessor to numerically compensate the sample measurement value based on the appropriate compensation value to obtain and output an accurate sample magnitude value.

7. The sensing method of claim 6, wherein the step (8) further comprises:
(81) enabling an operational amplifier to receive the electrochemical reaction signal and convert the electrochemical reaction signal into a second voltage signal; and
(82) enabling a first A/D converter to receive the second voltage signal and convert the second voltage signal into the second digital signal.

* * * * *